(12) United States Patent
Sugahara et al.

(10) Patent No.: US 9,775,799 B2
(45) Date of Patent: Oct. 3, 2017

(54) MICRONEEDLE-COATING COMPOSITION AND MICRONEEDLE DEVICE

(71) Applicant: HISAMITSU PHARMACEUTICAL CO., INC., Tosu-shi, Saga (JP)

(72) Inventors: Takuya Sugahara, Tsukuba (JP); Kazuya Machida, Tsukuba (JP)

(73) Assignee: HISAMITSU PHARMACEUTICAL CO., INC., Tosu-Shi, Saga (JP)

( * ) Notice: Subject to any disclaimer, the term of this patent is extended or adjusted under 35 U.S.C. 154(b) by 0 days.

(21) Appl. No.: 14/766,893

(22) PCT Filed: Feb. 12, 2014

(86) PCT No.: PCT/JP2014/053197
§ 371 (c)(1),
(2) Date: Aug. 10, 2015

(87) PCT Pub. No.: WO2014/126104
PCT Pub. Date: Aug. 21, 2014

(65) Prior Publication Data
US 2015/0374620 A1    Dec. 31, 2015

(30) Foreign Application Priority Data
Feb. 13, 2013  (JP) .............................. P2013-025954

(51) Int. Cl.
*A61K 38/00* (2006.01)
*A61K 9/00* (2006.01)
(Continued)

(52) U.S. Cl.
CPC ............ *A61K 9/0021* (2013.01); *A61K 47/02* (2013.01); *A61K 47/12* (2013.01); *A61K 47/183* (2013.01);
(Continued)

(58) Field of Classification Search
CPC ........ A61K 38/00; A61K 47/02; A61K 47/12; A61K 47/183; A61K 9/0021;
(Continued)

(56) References Cited

U.S. PATENT DOCUMENTS

| 4,839,341 A * | 6/1989 | Massey ................ A61K 9/0019 514/494 |
| 2005/0106209 A1 | 5/2005 | Ameri et al. |

(Continued)

FOREIGN PATENT DOCUMENTS

| CN | 1901841 A | 1/2007 |
| CN | 102917722 A | 2/2013 |

(Continued)

OTHER PUBLICATIONS

Editing Tip: Parenthetical Elements [online] retrieved on Jun. 9, 2016 from: http://www.aje.com/en/arc/editing-tip-parenthetical-elements/; 5 pages.*

(Continued)

*Primary Examiner* — Ernst V Arnold
(74) *Attorney, Agent, or Firm* — Nath, Goldberg & Meyer; Joshua B. Goldberg; Tanya E. Harkins

(57) ABSTRACT

Disclosed is a microneedle coating composition comprising a physiologically active substance (excluding Japanese encephalitis vaccine antigen), a basic amino acid, and an acid, wherein the mole number of the acid for one mole of the basic amino acid is larger than $1/(N+1)$ and less than 2, where N represents the valence of the acid.

7 Claims, 5 Drawing Sheets

(51) Int. Cl.
  *A61K 47/12* (2006.01)
  *A61K 47/18* (2017.01)
  *A61L 31/16* (2006.01)
  *A61M 5/32* (2006.01)
  *A61K 47/02* (2006.01)
  *A61M 37/00* (2006.01)

(52) U.S. Cl.
  CPC ............ *A61L 31/16* (2013.01); *A61M 5/329* (2013.01); *A61M 37/0015* (2013.01); *A61K 38/00* (2013.01); *A61L 2300/214* (2013.01)

(58) Field of Classification Search
  CPC .............. A61L 2300/214; A61L 31/16; A61M 37/0015; A61M 5/329
  See application file for complete search history.

(56) References Cited

U.S. PATENT DOCUMENTS

2008/0213461 A1    9/2008  Gill et al.
2014/0330198 A1*  11/2014  Zhang .................. A61K 9/0021
                                                                604/46

FOREIGN PATENT DOCUMENTS

| JP | 2007511508 A | 5/2007 |
| JP | 2007527392 A | 9/2007 |
| JP | 2007536988 A | 12/2007 |
| JP | 2008528509 A | 7/2008 |
| WO | 2010/013601 A1 | 2/2010 |
| WO | 2011/150144 A2 | 12/2011 |

OTHER PUBLICATIONS

Ejima et al. (BioProcess International. 2005 pp. 20-22, 24, 26 and 28).*
International Patent Application No. PCT/JP2014/053197, International Search report dated Mar. 11, 2014, two (2) pages.
International Patent Application No. PCT/JP2014/053197, International Preliminary Report of Patentability dated Aug. 27, 2015, six (6) pages.
Schneider, Curtiss P. et al., "Arginine and the Hofmeister Series: The Role of Ion-Ion Interactions in Protein Aggregation Suppression", Journal of Pyysical Chemistry Part B: Condensed Matter, Materials, Surfaces Interfaces & Biophysical; vol. 115, No. 22, pp. 7447-7458, XP55300267, Jun. 9, 2011.
Supplementary European Search Report for EP 14751401.2, transmitted Sep. 15, 2016.

* cited by examiner (a)

(b)

(c)

MICRONEEDLE-COATING COMPOSITION AND MICRONEEDLE DEVICE

This is a National Phase Application filed under 35 U.S.C. 371 as a national stage of PCT/JP2014/053197, filed Feb. 12, 2014, an application claiming the benefit of Japanese Application No. P2013-025954, filed Feb. 13, 2013, the content of each of which is hereby incorporated by reference in its entirety.

TECHNICAL FIELD

The present invention relates to a microneedle coating composition and a microneedle device.

BACKGROUND ART

As a means for percutaneously administering an agent, a microneedle device is known. In some of such devices, a coating containing a drug and a thickener is formed (for example, Patent Literature 1).

In addition, a composition including a preparation composed of a biologically active substance and a viscosity-enhancing counterion (Patent Literature 2) and a coating formulation having a pH less than about 6 and containing at least one low-volatile counterion (Patent Literature 3) are known. Furthermore, a composition including a preparation composed of a therapeutically effective amount of a peptide agent and at least one counterion (Patent Literature 4) and a composition including a preparation composed of a biologically active ingredient and non-volatile counterion, having enhanced pH stability and solubility when dried (Patent Literature 5) are known. There is, in addition to these compositions, a coating containing a biological active substance and an additive, where a low content of an amino acid is used as an example of the additive (Patent Literature 6).

CITATION LIST

Patent literature

Patent Literature 1: US 2008/0213461 A1
Patent Literature 2: JP-T-2007-511508
Patent Literature 3: JP-T-2007-536988
Patent Literature 4: JP-T-2008-528509
Patent Literature 5: JP-T-2007-527392
Patent Literature 6: WO2011/150144

SUMMARY OF INVENTION

Technical Problem

However, it has been found that in Patent Literatures 1 and 2, the viscosity-increasing effect of the coating is insufficient even if the material exemplified as a thickener is contained and that it is difficult to hold a sufficient amount of a physiologically active substance necessary for administration in a coating composition when the coating composition is applied to the tip of a microneedle.

Accordingly, it is an object of the present invention to provide a microneedle coating composition having a sufficient viscosity and a microneedle device including a coating layer formed from the composition.

Solution to Problem

The microneedle coating composition of the present invention comprises a physiologically active substance (excluding Japanese encephalitis vaccine antigen), a basic amino acid, and an acid, wherein the mole number of the acid for one mole of the basic amino acid is larger than 1/(N+1) and less than 2, where N represents the valence of the acid.

By adjusting the mole number of the acid for one mole of the basic amino acid within the above-mentioned range, the basic amino acid can be dissolved in an aqueous solution at a high concentration (for example, 20% w/w or more) to provide a high-viscosity composition, and the composition can be controlled to desired shape and thickness when it is coated on a microneedle. Accordingly, a sufficient amount of a physiologically active substance necessary for administration can be held on a microneedle. When the mole number of the acid for one mole of the basic amino acid is 1/(N+1) or less, since the content of the acid in the coating composition is low, the coating composition cannot dissolve the basic amino acid. In contrast, when the mole number of the acid for one mole of the basic amino acid is 2 or more, since the content of the basic amino acid in the coating composition is reduced, the stability of the physiologically active substance is reduced. Accordingly, the coating composition allows the physiologically active substance contained therein to be stably present, by adjusting the numbers of moles of the acid for one mole of the basic amino acid within the above-mentioned range.

In the microneedle coating composition, the acid is preferably an acid having a melting point of 40° C. or more, more preferably at least one acid selected from the group consisting of phosphoric acid, lactic acid, benzoic acid, maleic acid, citric acid, tartaric acid, succinic acid, ascorbic acid, and aspartic acid, and most preferably at least one acid selected from the group consisting of phosphoric acid, citric acid, and tartaric acid. The use of such an acid can dissolve a larger amount of a basic amino acid in a coating composition. In addition, the concentration of the basic amino acid in the coating composition can be increased, and the stability of the physiologically active substance contained can be further improved.

In the microneedle coating composition, the basic amino acid is preferably arginine. The use of arginine as the basic amino acid can notably improve the stability of the physiologically active substance in the coating composition.

In the microneedle coating composition, the concentration of the basic amino acid is preferably 20% w/w or more based on the total mass of the microneedle coating composition. A content of the basic amino acid of 20% w/w or more can improve the stability of the physiologically active substance in the microneedle coating composition.

The viscosity of the microneedle coating composition at 25° C. is preferably 10 to 45000 mPa·s. By adjusting the viscosity within such a range, dripping when the microneedle is coated with the composition can be minimized to improve the yield of product.

The present invention also provides a microneedle device including a coating layer formed from the microneedle coating composition on a microneedle. Here, the coating layer is preferably formed on the tip portion of the microneedle and more preferably formed only on the tip portion of the microneedle.

Advantageous Effects of Invention

According to the present invention, a microneedle coating composition having a sufficient viscosity is provided. Application of the microneedle coating composition can provide a microneedle device in which a physiologically active substance as a drug is stabilized.

DESCRIPTION OF EMBODIMENTS

Preferred embodiments will now be described with reference to the drawings. Note that in the description of the drawings, the same elements are denoted by the same reference symbols, and the repeated description will be omitted. A part of the drawings is exaggeratedly drawn for easy understanding, and the dimensional ratios do not necessarily agree with those in the description.

Figure 1:
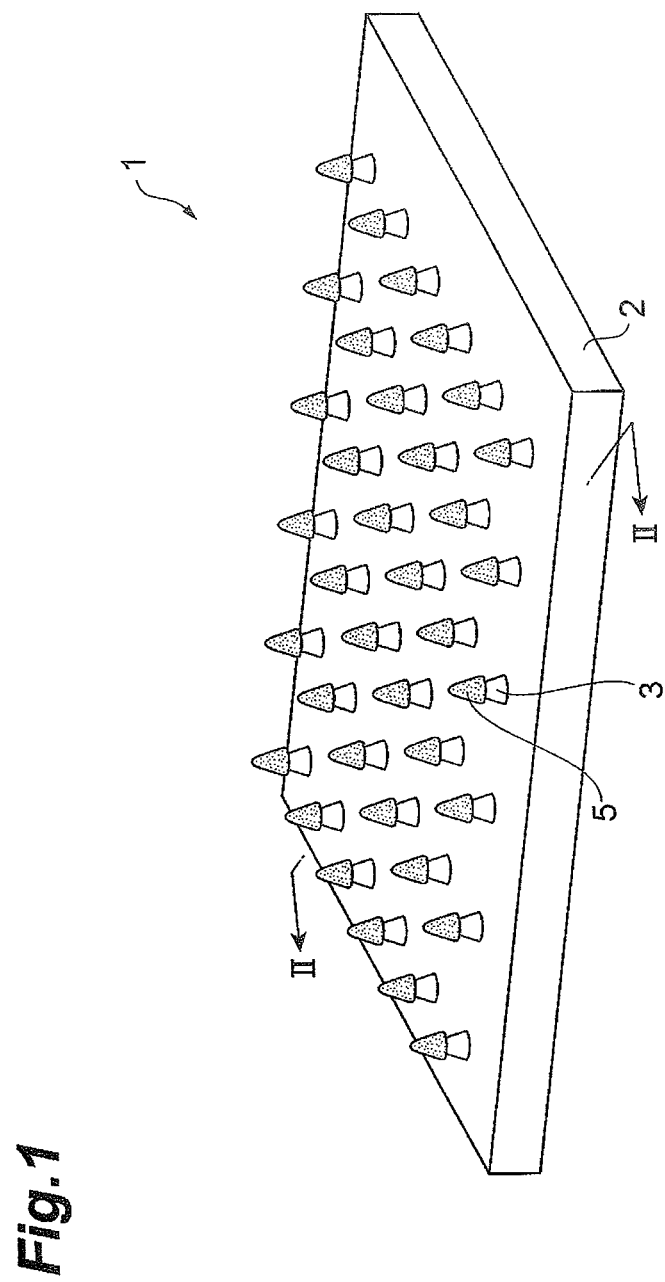
FIG. 1 is a perspective view illustrating an embodiment of a microneedle device.

FIG. 1 is a perspective view illustrating an embodiment of a microneedle device. The microneedle device 1 shown in FIG. 1 includes a substrate 2, a plurality of microneedles 3 two-dimensionally arranged on the substrate 2, and coating layers 5 disposed on the microneedles 3. The coating layers 5 are formed from the microneedle coating composition of the present invention, and it is preferable to remove at least part of the volatile component.

The substrate 2 is a base for supporting the microneedles 3. The area of the substrate 2 is preferably 0.5 to 10 $cm^2$, more preferably 1 to 5 $cm^2$, and further preferably 1 to 3 $cm^2$. A substrate having a desired size may be constituted by binding a plurality of the substrates 2.

The microneedles 3 each have a microstructure preferably having a height (length) of 50 to 600 μm. Here, the administration of the physiologically active substance (excluding Japanese encephalitis vaccine antigen, hereinafter, the simple term "physiologically active substance" referred to a physiologically active substance other than Japanese encephalitis vaccine antigen.) contained in the microneedle coating composition is ensured by adjusting the length of the microneedles 3 to 50 μm or more. In addition, by adjusting the length of the microneedles 3 to 600 μm or less, it is possible to prevent the microneedles from coming into contact with the nerves and thereby certainly reduce a risk of pain and to certainly prevent a risk of bleeding. In addition, when the lengths of the microneedles 3 are 500 μm or less, the physiologically active substance can be efficiently administered in an amount that should enter within the skin, and administration without perforating the basal membrane is possible. The lengths of the microneedles 3 are particularly preferably 300 to 500 μm.

Here, the microneedles 3 are each a convex structure and mean a structure in an acicular shape or including an acicular shape in a broad sense. The microneedle is not limited to acicular one having a sharp tip and may be one having a blunt tip. When the microneedle 3 has a conical structure, the diameter at the base is preferably about 50 to 200 μm. Although the microneedles 3 are conical in this embodiment, the shapes of the microneedles may be a polygonal pyramid, such as quadrangular pyramid, or another shape.

The microneedles 3 are typically disposed with spaces therebetween to give a density such that about one to ten microneedles are disposed for 1 millimeter (mm) of the row of the needles. In general, adjacent rows are apart from each other by a distance substantially the same as the space between the needles in a row, and the density of needles is 100 to 10000 needles per 1 $cm^2$. A density of 100 needles or more can efficiently perforate the skin. In contrast, a density exceeding 10000 needles is difficult to maintain the strength of the microneedles 3. The density of the microneedles 3 is preferably 200 to 5000 needles, more preferably 300 to 2000 needles, and further preferably 400 to 850 needles.

Examples of the material of the substrate 2 or the microneedles 3 include silicon, silicon dioxide, ceramic, metals (such as stainless steel, titanium, nickel, molybdenum, chromium, and cobalt), and synthetic or natural resin materials, and considering the antigenicity of the microneedle and the unit price of the material, the material is particularly preferably a biodegradable polymer, such as polylactic acid, polyglycolide, polylactic acid-co-polyglycolide, pullulan, capronolactone, polyurethane, or polyanhydrate, or a non-biodegradable polymer, for example, a synthetic or natural resin material, such as polycarbonate, polymethacrylic acid, ethylene vinyl acetate, polytetrafluoroethylene, or polyoxymethylene. In addition, polysaccharides, such as hyaluronic acid, sodium hyaluronate, pullulan, dextran, dextrin, and chondroitin sulfate, are also preferred.

Examples of the method of producing the substrate 2 or the microneedles 3 include a wet etching process and dry etching process using silicon substrates, precision machining using a metal or resin (such as electric discharge processing, laser processing, dicing processing, hot emboss processing, and injection molding processing), and mechanical cutting. The substrate 2 and microneedles 3 are integrally molded by these processing methods. Examples of a method for making the microneedles 3 hollow include a method involving making microneedles 3 and then subjecting the microneedles 3 to secondary processing with laser for example.

The microneedle device 1 includes a coating layers 5 on the microneedles 3, and it is preferable to form the coating layers 5 by application of a microneedle coating composition. Examples of the method of application include spray coating and dip coating, and the dip coating is preferred. In FIG. 1, although the coating layers 5 are formed on all the microneedles 3, the coating layers 5 may be formed only on a part of the plurality of microneedles 3. In addition, in FIG. 1, the coating layers 5 are formed only on the tip portions of the microneedles 3 but may be formed so as to cover the entire of each of the microneedles 3. Furthermore, the coating layers 5 may be formed on the substrate 2.

Figure 3:
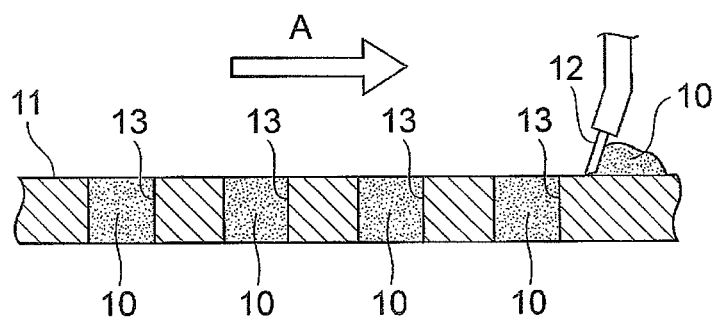
FIG. 3 includes diagrams (a), (b), and (c) illustrating an embodiment of a method of producing a microneedle device.
Figure 3:
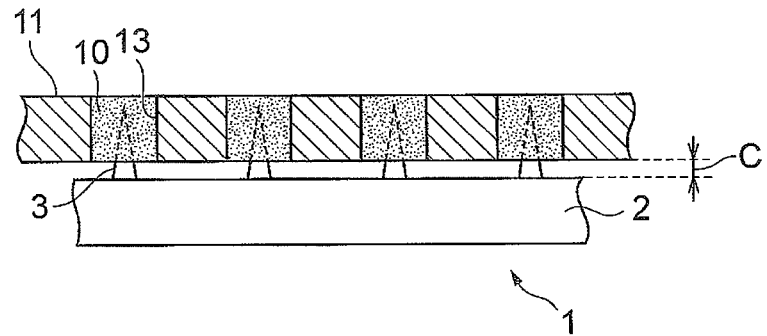
Figure 3:
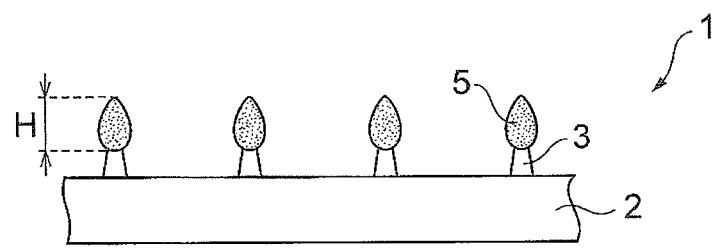

FIGS. 3(a), (b), and (c) are diagrams illustrating an embodiment of the method of producing a microneedle device 1. In this method, first, as shown in FIG. 3(a), the microneedle coating composition 10 is swept on a mask plate 11 with a spatula 12 in the direction of the arrow A. By doing so, opening portions 13 are filled with the microneedle coating composition 10. Subsequently, as shown in FIG. 3(b), microneedles 3 are inserted into the opening portions 13 of the mask plate 11. Subsequently, as shown in FIG. 3(c), the microneedles 3 are pulled out from the opening portions 13 of the mask plate 11. By doing so, the microneedle coating composition 10 is allowed to adhere onto the microneedles 3. The microneedle coating composition 10 may adhere onto the substrate 2. Subsequently, the volatile component in the microneedle coating composition 10 on the microneedles 3 is removed by a method, i.e., air drying, vacuum drying, combination thereof, or the like. By doing so, the coating layers 5 rigidly adhere onto the microneedles 3 and typically become into a glassy or solid shape to produce a microneedle device 1. The moisture content of the coating layers 5 is usually 55% by mass or less, preferably 30% by mass or less, and more preferably 10% by mass or less, based on the total mass of the coating layers 5. The above-described method prevents the adhering microneedle coating composition 10 from dripping. The term dripping refers to flowing of the coating composition from the needle tip and means that the H portion in FIG. 3(c) gets longer.

The heights H of the coating layers 5 adhering to the microneedles 3 are adjusted by the clearance (gap) C shown in FIG. 3(b). This clearance C is defined by the distance from the bases of the microneedles 3 to the surface of the mask plate 11 (the thickness of the substrate 2 is not involved in the clearance C), and is determined depending on the tension of the mask plate 11 and the lengths of the microneedles 3. The range of the distance of the clearance C is preferably 0 to 500 μm. When the distance of the clearance C is zero, it means that the microneedle coating composition 10 is applied to the entire of each of the microneedle 3. The height H of the microneedle coating composition 10 adhering onto each of the microneedles 3 varies depending on the height of the microneedle 3 and can be 0 to 500 μm, usually 10 to 500 μm, preferably about 30 to 300 μm, and particularly preferably about 40 to 250 μm. In order to effectively use the physiologically active substance in the microneedle coating composition 10, it is preferable to localize the microneedle coating composition 10 at a part of each of the microneedles, i.e., the tip portion of the needle, and also from the viewpoint of stimulation of the skin and the transfer ratio of a drug to the skin, it is preferable to localize the composition 10 in the area of 200 μm from the tip. Since the microneedle coating composition 10 allows a basic amino acid to be dissolved in an aqueous solution at a high concentration (for example, 20% w/w or more) and has a high viscosity, it is possible to form the coating layers 5 on a part of each of the microneedles. The microneedle coating composition 10 held on the microneedle 3 in such a form can form a coating layer 5, preferably, in a nearly spherical or droplet shape, on the tip portion of the microneedle 3, after removal of the volatile component, and is inserted into the skin simultaneously when the microneedle 3 is punctured into the skin.

The thickness of each of the coating layers 5 adhering on the microneedles 3 after drying is preferably less than 50 μm, more preferably less than 40 μm, and further preferably 1 to 30 μm. In general, the thickness of the coating layer 5 adhering to the microneedle is the average of the thicknesses measured over the surface of the microneedle 3 after drying. The thickness of each of the coating layers 5 adhering on the surface of the microneedles 3 can be increased by applying a plurality of coating films of the microneedle coating composition 10, that is, by repeating the adhering step after adhesion of the microneedle coating composition 10.

In adhesion of the microneedle coating composition 10 to the microneedles 3, it is preferable to maintain the temperature and humidity of the installation environment of the apparatus constant. In addition, when the microneedle coating composition 10 comprises water, the environment can be filled with water, as needed. By doing so, transpiration of the water in the microneedle coating composition 10 can be prevented as much as possible.

Figure 2:
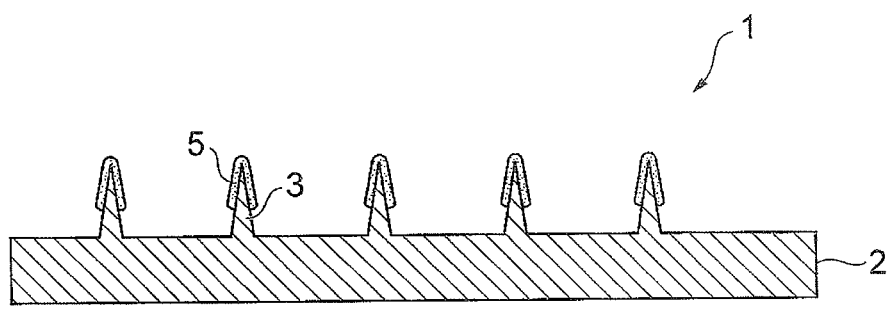
FIG. 2 is a cross-sectional view taken along the line of FIG. 1.

FIG. 2 is a cross-sectional view taken along the line II-II of FIG. 1. As shown in FIG. 2, the microneedle device 1 includes a substrate 2, microneedles 3 disposed on the substrate 2, and coating layers 5 disposed on the microneedles 3. The coating layers 5 adhering to the microneedles comprise a physiologically active substance, a basic amino acid, and an acid and can be produced, for example, through the above-described process.

The microneedle coating composition 10 comprises a physiologically active substance, a basic amino acid, and an acid, wherein the mole number of the acid for one mole of the basic amino acid is larger than 1/ (N+1) and less than 2, where N represents the valence of the acid. The mole number of the acid for one mole of the basic amino acid is preferably 1/ N or more and 1 or less.

The term physiologically active substance used in the present invention includes drugs that are used for all therapy in the medical field. Examples of the physiologically active substance include prophylactic drugs (antigens), anti-infective agents such as antibiotics and antiviral agents, analgesics, analgesic combinations, anesthetics, anorectics, antiarthritic agents, antiasthmatic agents, anticonvulsants, antidepressants, antidiabetic agents, antidiarrheal agents, antihistamines, anti-inflammatory agents, antimigraine preparations, anti-motion sickness drugs, antinauseants, antineoplastics, antiparkinsonism drugs, antipruritics, antipsychotics, antipyretics, antispasmodics including those for the stomach and intestines and the urinary tract, anticholinergic agents, sympathomimetics, xanthine derivatives, cardiovascular preparations including calcium channel blockers, beta-blockers, beta-agonists, antiarrhythmics, antihypertensives, ACE inhibitors, diuretics, vasodilators including general coronary, peripheral, and cerebral blood vessels, central nervous system stimulants, cough and cold preparations, decongestants, diagnostic agents, hormones, hypnotics, immunosuppressives, muscle relaxants, parasympatholytics, parasympathomimetic agents, prostaglandin, protein, peptides, polypeptides, psychostimulants, sedatives, and tranquilizers.

The antigens are not particularly limited and may be polynucleotides (DNA vaccines and RNA vaccines), peptide antigens, and protein-based vaccines. Specifically, examples of the antigens include protein, polysaccharides, oligosaccharides, lipoprotein, attenuated or inactivated viruses such as cytomegalovirus, hepatitis B virus, hepatitis C virus, human papillomavirus, rubella virus, and varicella zoster virus, attenuated or inactivated bacteria such as *Bordetella pertussis, Clostridium tetani, Corynebacterium diphtheriae,* Group A *streptococcus, Legionella pneumophila, Neisseria meningitidis, Pseudomonas aeruginosa, Streptococcus pneumoniae, Treponema pallidum*, and *Vibrio cholerae*, and antigens in a form of mixture thereof. The term "antigen" includes a large number of commercially available vaccines containing antigenic active substances, such as flu vaccines, Lyme disease vaccine, rabies vaccine, measles vaccine, mumps vaccine, chickenpox vaccine, smallpox vaccine, hepatitis vaccine, pertussis vaccine, and diphtheria vaccine, and also antigens that are used in vaccine therapy for cancer, arteriosclerosis, nervous disease, Alzheimer's disease, and so on. In addition, the antigen may be an allergenic material having antigenicity (sensitivity), such as a variety of metals and chemicals. For example, in an allergy test for clarifying the antigen of atopic dermatitis and therapy thereof, house dusts such as dust and inactivated mites, various types of pollen, and so on may be used. In addition, examples of the antigen include antigens recognized by inflammatory T cells involved in T-cell-mediated interstitial autoimmune disease or symptoms.

The concentration of the physiologically active substance in the microneedle coating composition 10 is preferably 0.01 to 50% w/w, and more preferably 0.1 to 40% w/w, based on the total mass of the microneedle coating composition 10. If the concentration of the physiologically active substance is 0.01% w/w or more, in the administration to the skin, an effective amount of the physiologically active substance can be released inside the skin to exhibit a sufficient drug efficacy.

The basic amino acid is not particularly limited and is one or more of, for example, lysine, histidine, arginine, ornithine, and carnitine and is preferably a free form thereof. In particular, from the point of broadening the selection range of the acid, at least one selected from the group consisting of lysine, histidine, and arginine is preferred, and arginine is more preferred.

The concentration of the basic amino acid in the microneedle coating composition 10 is preferably 20% w/w or more, more preferably 30% w/w or more, and further preferably 40% or more, based on the total mass of the microneedle coating composition 10, from the viewpoint of the viscosity. A content of the basic amino acid of 20% w/w or more can improve the stability of the physiologically active substance in the microneedle coating composition 10. A concentration of the basic amino acid of 70% w/w or less makes the handling in the application to the microneedles 3 easy.

In addition, the concentration of the basic amino acid in the coating layers 5 prepared by applying the microneedle coating composition 10 to the microneedles 3 and removing the volatile component is preferably 40% w/w or more based on the total mass of the coating layer 5. In addition, the ratio of the concentration of the basic amino acid in the coating layers 5 to the concentration of basic amino acid in the microneedle coating composition 10 (concentration of the basic amino acid in the coating layers 5/concentration of basic amino acid in the microneedle coating composition 10) is preferably 4.5 or less, more preferably 3 or less, and further preferably 2 or less. When the ratio is 4.5 or less, the microneedle coating composition 10 can be easily applied to the microneedles 3, and the stability of the physiologically active substance in the coating layers 5 can be improved.

The acid in the microneedle coating composition 10 is preferably an acid having a melting point of 40° C. or more. The use of such an acid allows the basic amino acid to be present at a high concentration (for example, 20% w/w or more) in the microneedle coating composition 10 and can improve the stability of the physiologically active substance in the microneedle coating composition 10. In particular, the acid is preferably at least one acid selected from the group consisting of phosphoric acid, lactic acid, benzoic acid, maleic acid, citric acid, tartaric acid, succinic acid, ascorbic acid, and aspartic acid, and more preferably at least one acid selected from the group consisting of phosphoric acid, citric acid, and tartaric acid. The concentration of the acid in the microneedle coating composition 10 is preferably 5% to 50% w/w and more preferably 10% to 30% w/w based on the total mass of the microneedle coating composition 10. The combination of the basic amino acid and the acid becomes into an amorphous state after drying. Furthermore, since the basic amino acid and the acid are low molecular, prompt solubilization of the coating layers 5 can be expected when the microneedles 3 are punctured into the skin.

The microneedle coating composition 10 may comprise, in addition to the physiologically active substance, the basic amino acid, and the acid, an aqueous solution, for example, purified water, physiological saline, or a buffer such as phosphate buffer, citrate buffer, acetate buffer, citrate-phosphate buffer, tris-hydrochloric acid buffer, or glycine-sodium hydroxide buffer. The content of these aqueous solutions is preferably 5% to 75% by mass based on the total mass of the microneedle coating composition 10. A content exceeding 75% by mass tends not to obtain a sufficient viscosity during coating, and a content of less than 5% by mass tends to make the dissolution of the composition difficult.

The microneedle coating composition 10 may comprise, in addition to the above-mentioned basic amino acid, a pharmaceutically acceptable salt of lysine. The addition of a pharmaceutically acceptable salt of lysine can further improve the stability of the physiologically active substance.

The pharmaceutically acceptable salt of lysine is preferably hydrochloride. The concentration of lysine hydrochloride may be 0.1% to 20% w/w based on the total mass of the microneedle coating composition 10. In a concentration exceeding 20% w/w, lysine hydrochloride may not be dissolved, and in a concentration of less than 0.1% w/w, the stability of the physiologically active substance may be insufficient.

In addition, the microneedle coating composition 10 may further comprise a polymer carrier (thickener) as an optional component. Examples of the polymer carrier include polyethylene oxide, polyhydroxymethyl cellulose, hydroxypropyl cellulose, polyhydroxypropyl methylcellulose, polymethyl cellulose, dextran, polyethylene glycol, polyvinyl alcohol, polyvinylpyrrolidone, pullulan, carmellose sodium, chondroitin sulfate, hyaluronic acid, dextran, and gum arabic. The weight-average molecular weight of polyethylene glycol used as the polymer carrier is preferably higher than 600 and not higher than 500000.

The polymer carrier is preferably a carrier having a high compatibility (uniform miscibility) with the physiologically active substance, and particularly preferred examples are hydroxypropyl cellulose, dextran, polyvinyl alcohol, and pullulan.

The content of the polymer carrier in the microneedle coating composition 10 is 0.005% to 30% by mass, preferably 0.01% to 20% by mass, and more preferably 0.05% to 10% by mass, based on the total mass of the microneedle coating composition 10. In addition, this polymer carrier needs to have a certain degree of viscosity for preventing dripping in some cases, and the viscosity at room temperature (25° C.) is preferably 100 to 100000 mPa·s. More preferred viscosity is 500 to 60000 mPa·s.

In addition to the description above, the microneedle coating composition 10 may comprise, as needed, a solubilizing agent or absorption promoter, such as propylene carbonate, crotamiton, L-menthol, peppermint oil, limonene, or diisopropyl adipate, a drug effect auxiliary agent, such as methyl salicylate, glycol salicylate, L-menthol, thymol, peppermint oil, nonylic acid vanillylamide, or capsicum extract.

Furthermore, as needed, the microneedle coating composition 10 may comprise a compound such as a stabilizer, an antioxidant, an emulsifier, a surfactant, or a salt. The surfactant may be a nonionic surfactant or an ionic surfactant (cationic, anionic, or zwitterionic), and is desirably a nonionic surfactant that is usually used as a medicinal base, from a safety standpoint. Examples of these compounds include sugar alcohol fatty acid esters, such as sucrose fatty acid ester, propylene glycol fatty acid ester, polyoxyethylene sorbitan fatty acid ester, polyoxyethylene sorbitan fatty acid ester, polyoxyethylene glycerin fatty acid ester, polyethylene glycol fatty acid ester, polyoxyethylene castor oil, and polyoxyethylene hydrogenated castor oil.

Other known preparation auxiliary materials may be contained in the microneedle coating composition 10, as long as they do not adversely affect the effect of improving the solubility and the viscosity of the microneedle coating composition 10 and do not adversely affect the characteristics and the physical properties of the dried microneedle coating composition 10 adhering to the microneedles 3.

The microneedle coating composition 10 needs to have a certain degree of viscosity for preventing dripping after application onto the microneedles 3. In the present invention, the addition of an acid to the basic amino acid allows the microneedle coating composition 10 to be blended with the basic amino acid at a high concentration (for example, 20% w/w or more) and can improve the viscosity. The viscosity is specifically about 100 to 45000 mPa·s, and in the coating composition having a viscosity within this range, a desired amount of the microneedle coating composition 10 is allowed to adhere to the microneedles 3 at a time and to localize at the tip portions of the microneedles 3, without depending on the material of the microneedles. Furthermore, in such a viscosity, approximately spherical or teardrop-shaped coating layers 5 can be formed on the tip portions of the microneedles 3, and a sufficient amount of a physiologically active substance can be held.

When the viscosity of the microneedle coating composition 10 at 25° C. is 45000 mPa·s or less, the shear stress is increased to increase the resistance to peeling between materials. Consequently, in application of a drug solution by a dipping method, the property (aggregability) of individuals, i.e., resistance to dissociation from the microneedles, is enhanced, and a larger amount of coating composition can be held on the microneedles. In contrast, if the viscosity exceeds 45000 mPa·s, the content of the physiologically active substance in the coating composition adhering to the microneedles shifts to a decrease, which is economically disadvantageous. When the viscosity of the coating composition is 100 mPa·s or more, since the aggregability is high, it is possible to hold the coating composition on the microneedles. Based on these characteristics, the viscosity of the microneedle coating composition 10 at 25° C. is preferably 100 to 45000 mPa·s, more preferably 300 to 35000 mPa·s, further preferably 500 to 30000 mPa·s, and particularly preferably 600 to 15000 mPa·s.

EXAMPLES

The present invention will now be more specifically described with reference to Examples of the present invention, but is not limited to these Examples, and can be variously modified within a scope not departing from the technical idea of the present invention.

<Solubility of Mixture of Arginine and Acid in Water>

Arginine was mixed with any of the acids (N valence) shown in Tables 1 to 3 at a ratio, arginine:acid=N:1; purified water was added to each mixture to prepare a dilute solution of 20% w/w arginine-acid; and the water was evaporated by lyophilization to make a lyophilized solid. Purified water was added to this lyophilized solid at a ratio, (the mixture (Arg+acid) of arginine and the acid):water=7:3, to prepare a concentrated solution of the mixture (Arg+acid) of arginine and the acid. In the tables, "solubility" shows the results, wherein the symbol "○" denotes a case in which a concentrated solution could be prepared with complete solubility, and the symbol "Δ" denotes a case in which a part of the lyophilized solid was partially dissolved.

TABLE 1

| | Inorganic acid | | | |
|---|---|---|---|---|
| | Hydrochloric acid (monovalent) | Sulfuric acid (divalent) | Methanesulfonic acid (monovalent) | Phosphoric acid (bivalent) |
| Melting point (° C.) | −27.3 | 10 | 20 | 42.4 |
| Solubility | Δ | Δ | Δ | ○ |

TABLE 2

| | Organic acid | | | | |
|---|---|---|---|---|---|
| | Glacial acetic acid (monovalent) | Lactic acid (monovalent) | Benzoic acid (monovalent) | Maleic acid (divalent) | Citric acid (trivalent) |
| Melting point (° C.) | 16.7 | 53 | 122 | 131 | 153 |
| Solubility | Δ | ○ | ○ | ○ | ○ |

TABLE 3

| | Organic acid | | | |
|---|---|---|---|---|
| | Tartaric acid (divalent) | Succinic acid (divalent) | Ascorbic acid (monovalent) | Aspartic acid (monovalent) |
| Melting point (° C.) | 168 | 185 | 190 | 300 |
| Solubility | ○ | ○ | ○ | ○ |

<Solubility in Water and Viscosity Characteristics of Mixture of Arginine and Acid Depending on Blending Ratio>

Arginine and an acid were mixed at the molar ratios shown in Table 4 and 5; purified water was added to each mixture to prepare a dilute solution of 20% w/w arginine-acid; and the water was evaporated by lyophilization to make a lyophilized solid. Purified water was added to this lyophilized solid at a ratio, (the mixture (Arg+acid) of arginine and the acid):water=7:3, to prepare a concentrated solution of the mixture (Arg+acid) of arginine and the acid. In the tables, "solubility" shows the results, wherein the symbol "○" denotes a case in which a concentrated solution could be prepared with complete solubility, the symbol "Δ" denotes a case in which the lyophilized solid was partially dissolved, and the symbol "×" denotes a case in which the lyophilized solid was not substantially dissolved. In the tables, the "viscosity" was measured with a small sample viscometer (VROC, manufactured by RheoSense, Inc.), and the unit thereof is "mPa·s".

In addition, the concentrated solution of each of the mixtures of arginine and an acid (Arg+acid, arginine:phosphoric acid=2:1, arginine:citric acid=3:1, and arginine:tartaric acid=2:1) was applied to a microneedles (height: about 500 μm, density: 640 needles/cm², shape: quadrangular pyramid), and the needle tips of the microneedles were observed with a microscope (VH-8000, manufactured by KEYENCE Corporation). The results of the observation showed that coating layers were formed on the tip portions of the microneedles and demonstrated that the mixtures of arginine and an acid are suitable for application to needle tips.

In addition, the viscosity of a saturated arginine aqueous solution (15% by mass of arginine) at 25° C. is merely 1.7 mPa·s, and when the saturated arginine aqueous solution is applied to microneedles, dripping is caused to prevent formation of coating layers on the tip portions of the microneedles.

TABLE 4

| Arg:Phosphoric acid (bivalent) | Solubility | Viscosity | Arg:Citric acid (trivalent) | Solubility | Viscosity |
| --- | --- | --- | --- | --- | --- |
| 1:1 | ○ | — | 1:1 | ○ | — |
| 2:1 | ○ | 1134 | 2:1 | ○ | — |
| 3:1 | ○ | — | 3:1 | ○ | 1331 |
| 4:1 | Δ | — | 4:1 | Δ | — |

TABLE 5

| Arg:Tartaric acid (divalent) | Solubility | Viscosity | Arg:Lactic acid (monovalent) | Solubility | Viscosity |
| --- | --- | --- | --- | --- | --- |
| 1:1 | ○ | — | 1:1 | ○ | — |
| 2:1 | ○ | 792 | 2:1 | Δ | — |
| 3:1 | Δ | — | 3:1 | X | — |
| 4:1 | X | — | 4:1 | X | — |

<Solubility of Mixture of Basic Amino Acid and Acid in Water>

Histidine (His) and lysine (Lys) were used as basic amino acids. In accordance with the procedure of preparing a concentrated solution of the mixture (Arg+acid) of arginine and the acid, a basic amino acid and an acid were mixed at a molar ratio of 1:1 to prepare concentrated solutions of a mixture (His+acid) of histidine and an acid and concentrated solutions of a mixture (Lys+acid) of lysine and an acid. In Tables 6 and 7, "Solubility" shows the results, wherein the symbol "○" denotes that a concentrated solution can be prepared with complete solubility.

TABLE 6

| His:citric acid (bivalent) | Solubility | His:tartaric acid (divalent) | Solubility |
| --- | --- | --- | --- |
| 1:1 | ○ | 1:1 | ○ |

| His:aspartic acid (monovalent) | Solubility | His:ascorbic acid (monovalent) | Solubility |
| --- | --- | --- | --- |
| 1:1 | ○ | 1:1 | ○ |

TABLE 7

| Lys:citric acid (trivalent) | Solubility | Lys:tartaric acid (divalent) | Solubility |
| --- | --- | --- | --- |
| 1:1 | ○ | 1:1 | ○ |

| Lys:aspartic acid (monovalent) | Solubility | Lys:ascorbic acid (monovalent) | Solubility |
| --- | --- | --- | --- |
| 1:1 | ○ | 1:1 | ○ |

<Evaluation of Stability of Physiologically Active Substance>

A test of evaluating the stability of a physiologically active substance for an aqueous solution comprising arginine (basic amino acid) and an acid was performed in accordance with the following procedure.

First, arginine and an acid were mixed at a specific molar ratio, and water was added to this mixture such that the concentration of the mixture was 5.6% w/w to prepare a coating composition. Subsequently, an aqueous solution of a physiologically active substance, 500 μg/mL of insulin (IRI) or 5 mg/mL of human growth hormone (hGH), was added to the coating composition such that the mass ratio of the aqueous solution of the mixture and the aqueous solution of the physiologically active substance was 9:1 to obtain a physiologically active substance-containing coating composition of which the concentration of the mixture is 50% w/w. Subsequently, this physiologically active substance-containing coating composition was applied to microneedles (height: about 500 μm, density: 640 needles/cm$^2$, shape: quadrangular pyramid) to provide 2.5 ng of IRI or 10 ng of hGH for one sheet of the microneedles, followed by drying at 37° C. for 30 minutes to make a microneedle device applied with the physiologically active substance. The stability of the physiologically active substance was evaluated by wrapping this microneedle device with an aluminum package and preserving it under a condition of 50° C. for one week.

Figure 4:
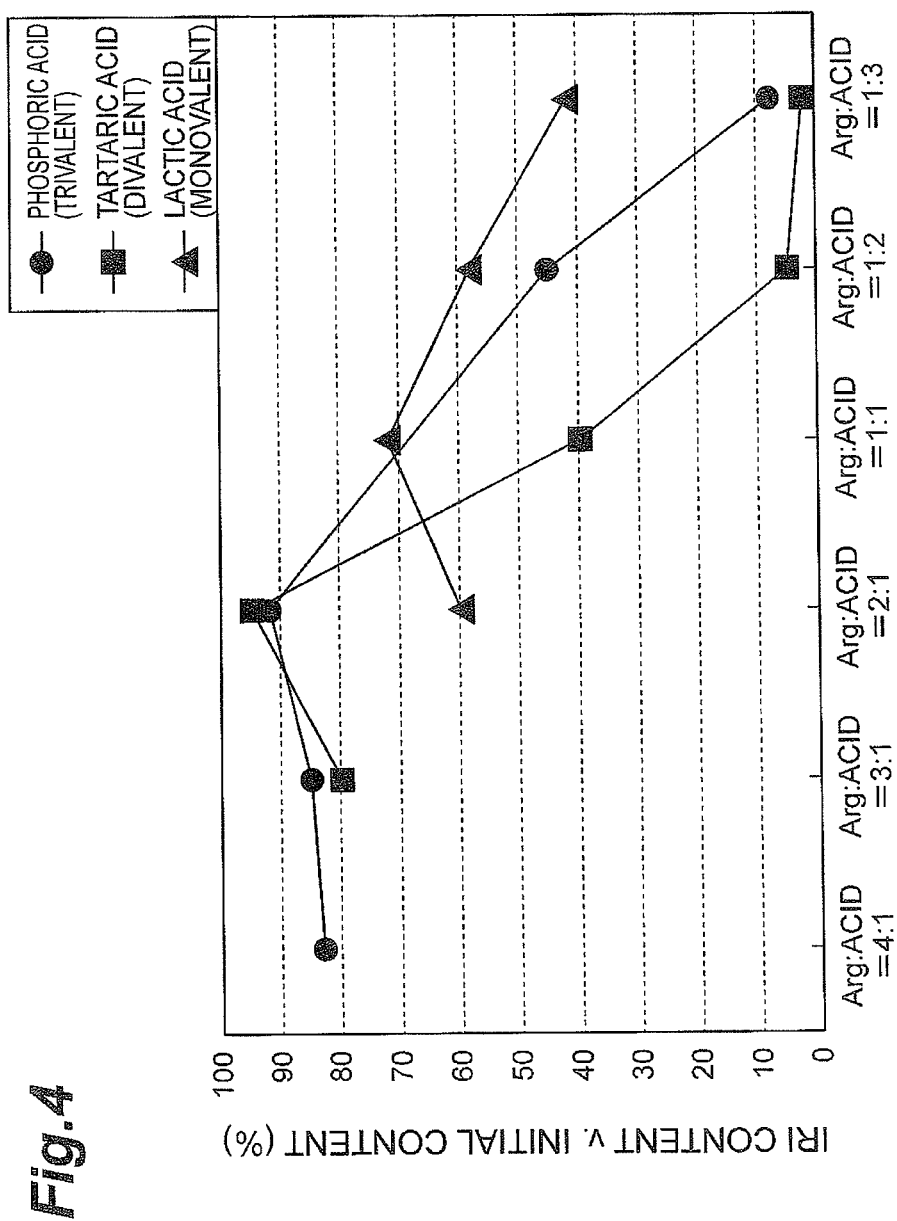
FIG. 4 is a graph showing stability of insulin in an aqueous solution containing arginine and an acid at a specific molar ratio.
Figure 5:
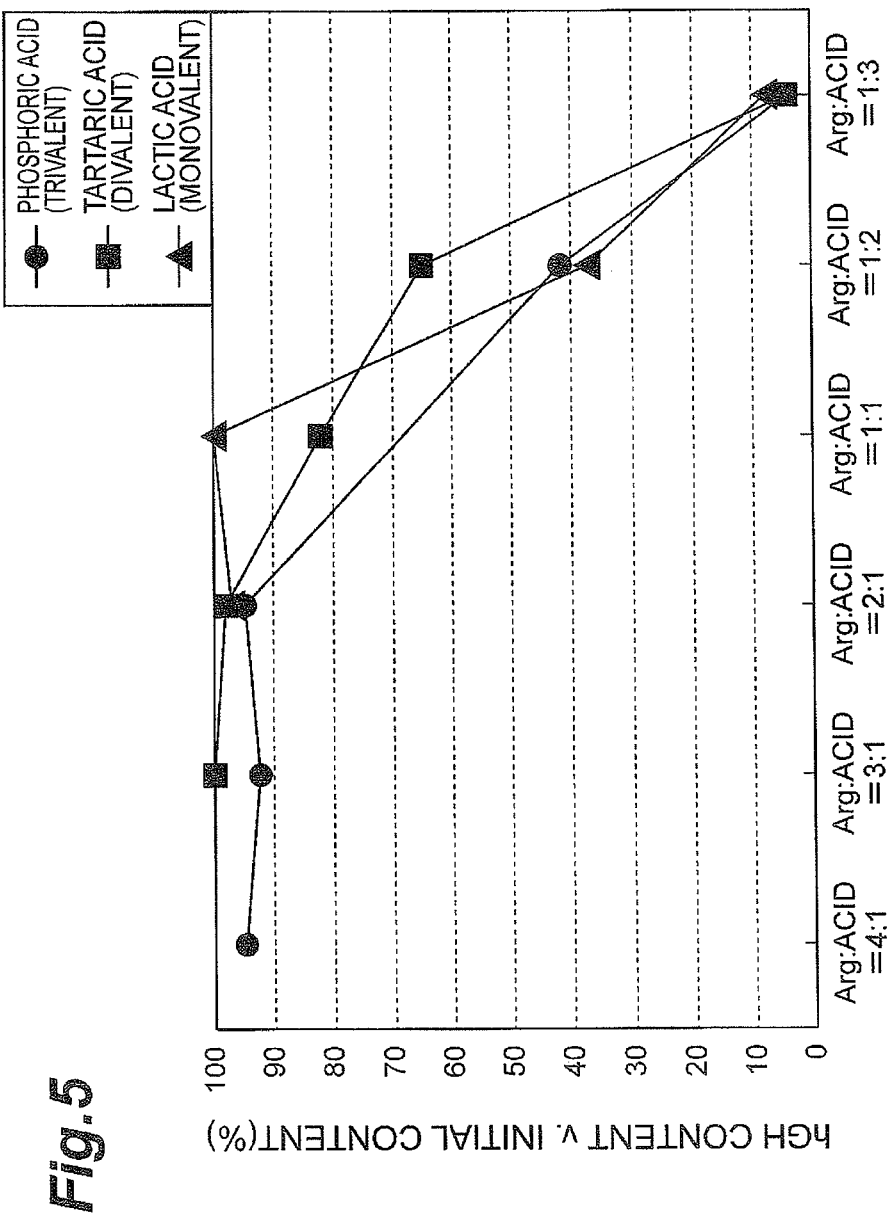
FIG. 5 is a graph showing stability of growth hormone in an aqueous solution containing arginine and an acid at a specific molar ratio.

The test of evaluating the stability of the physiologically active substance was performed with AIA (fully automated enzyme immunoassay analyzer, manufactured by Tosoh Corporation), and evaluation was performed by defining the initial content of the physiologically active substance before the start of the test as 100% by mass and measuring the relative content after one week. FIG. 4 is a graph showing stability of insulin in an aqueous solution containing arginine and an acid at a specific molar ratio. FIG. 5 is a graph showing stability of growth hormone in an aqueous solution containing arginine and an acid at a specific molar ratio. As the acid, phosphoric acid (trivalent), tartaric acid (divalent), and lactic acid (monovalent) were used.

REFERENCE SIGNS LIST

1: microneedle device, 2: substrate, 3: microneedle, 5: coating layer, 10: microneedle coating composition, 11: mask plate, 12: spatula, 13: opening portion

The invention claimed is:

1. A microneedle coating composition comprising:
   a physiologically active substance excluding Japanese encephalitis vaccine antigen;
   a basic amino acid in a concentration of 30% w/w or more based on the total mass of the microneedle coating composition; and
   an acid in a concentration of 5% to 50% w/w based on the total mass of the microneedle coating composition, wherein the acid is at least one acid selected from the group consisting of phosphoric acid, lactic acid, benzoic acid, maleic acid, citric acid, tartaric acid, succinic acid, ascorbic acid and aspartic acid, wherein
   a mole number of the acid for one mole of the basic amino acid is larger than 1/(N+1) and less than 2, where N represents a valence of the acid.

2. The microneedle coating composition according to claim 1, wherein the acid has a melting point of 40° C. or more.

3. The microneedle coating composition according to claim 1, wherein
   a viscosity of the composition at 25° C. is 100 to 45000 mPa·s.

4. A microneedle device comprising:
   a microneedle; and
   a coating layer formed from the microneedle coating composition according to claim 1 on the microneedle.

5. The microneedle device according to claim 4, wherein the coating layer is formed on a tip portion of the microneedle.

6. The microneedle coating composition according to claim 1, wherein the basic amino acid is arginine.

7. A microneedle device comprising:
   a microneedle; and
   a coating layer formed from the microneedle coating composition according to claim 6 on the microneedle.

* * * * *